United States Patent
Overweg et al.

(10) Patent No.: US 8,604,795 B2
(45) Date of Patent: *Dec. 10, 2013

(54) SPLIT GRADIENT COIL AND PET/MTI HYBRID SYSTEM USING THE SAME

(75) Inventors: Johan A. Overweg, Uelzen (DE); Volkmar Schulz, Wuerselen (DE); Torsten Solf, Aachen (DE); Gordon D. Demeester, Wickliffe, OH (US); Michael A. Morich, Mentor, OH (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/489,491

(22) Filed: Jun. 6, 2012

(65) Prior Publication Data
US 2012/0241631 A1    Sep. 27, 2012

Related U.S. Application Data

(62) Division of application No. 12/531,979, filed as application No. PCT/IB2008/050151 on Jan. 16, 2008, now Pat. No. 8,334,697.

(60) Provisional application No. 60/910,032, filed on Apr. 4, 2007.

(51) Int. Cl.
*G01V 3/00* (2006.01)

(52) U.S. Cl.
USPC ............................ 324/328; 324/322

(58) Field of Classification Search
USPC .......................... 324/318, 322, 319
See application file for complete search history.

(56) References Cited

U.S. PATENT DOCUMENTS

| 5,331,281 | A |   | 7/1994 | Otsuka |
|---|---|---|---|---|
| 5,378,989 | A | * | 1/1995 | Barber et al. ............ 324/318 |
| 5,389,909 | A |   | 2/1995 | Havens |
| 5,585,724 | A |   | 12/1996 | Morich et al. |
| 5,696,449 | A |   | 12/1997 | Boskamp |

(Continued)

FOREIGN PATENT DOCUMENTS

| JP | 08038443 A | 2/1996 |
|---|---|---|
| JP | 2004298303 A | 10/2004 |

(Continued)

OTHER PUBLICATIONS

Handler, W. B., et al.; Simulation of scattering and attenuation of 511 keV photons in a combined PET/field-cycled MRI system; 2006; Phys. Med. Biol.; 51:2479-2491.

(Continued)

*Primary Examiner* — Louis Arana

(57) ABSTRACT

A generally cylindrical set of coil windings includes primary coil windings and shield coil windings at a larger radial position than the primary coil windings, and an arcuate or annular central gap that is free of coil windings, has an axial extent of at least ten centimeters, and spans at least a 180° angular interval. Connecting conductors disposed at each edge of the central gap electrically connect selected primary and secondary coil windings. In a scanner setting, a main magnet is disposed outside of the generally cylindrical set of coil windings. In a hybrid scanner setting, an annular ring of positron emission tomography (PET) detectors is disposed in the central gap of the generally cylindrical set of coil windings.

19 Claims, 10 Drawing Sheets

(56) References Cited

U.S. PATENT DOCUMENTS

Figure 1:
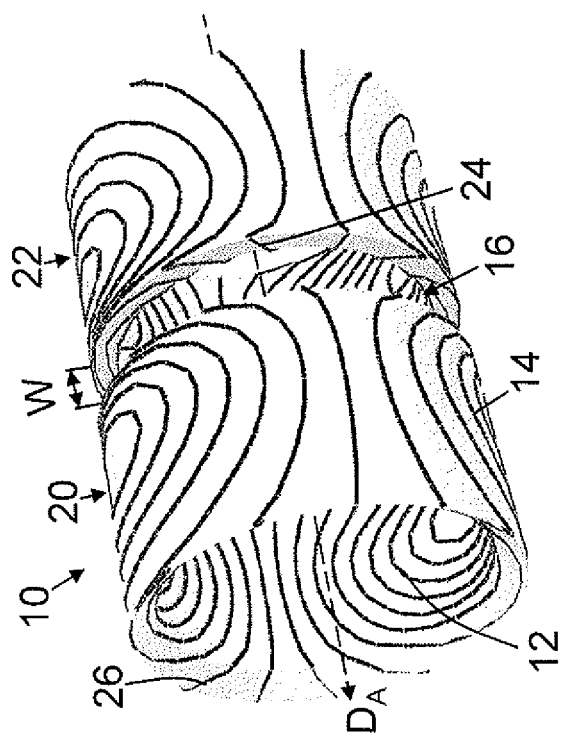

| | | |
|---|---|---|
| 5,773,976 A | 6/1998 | Sakakura et al. |
| 5,892,359 A | 4/1999 | Yui et al. |
| 5,952,830 A | 9/1999 | Petropoulos et al. |
| 6,100,780 A | 8/2000 | Dorri et al. |
| 6,549,010 B2 | 4/2003 | Roozen et al. |
| 6,591,127 B1 | 7/2003 | McKinnon |
| 6,842,005 B2 | 1/2005 | Schuster |
| 6,894,498 B2 | 5/2005 | Edelstein |
| 6,930,482 B2 | 8/2005 | Heid et al. |
| 7,053,616 B2 | 5/2006 | Roozen et al. |
| 7,160,288 B2 | 1/2007 | Sumiya |
| 2003/0090267 A1 | 5/2003 | Rubashov |
| 2004/0239327 A1 | 12/2004 | Heid et al. |
| 2005/0122106 A1 | 6/2005 | Ham et al. |
| 2006/0033496 A1 | 2/2006 | Shvartsman et al. |
| 2006/0293580 A1 | 12/2006 | Ladebeck et al. |
| 2009/0299170 A1* | 12/2009 | Gebhardt et al. ............. 600/411 |

FOREIGN PATENT DOCUMENTS

| | | |
|---|---|---|
| WO | 2005088330 A1 | 9/2005 |
| WO | 2006111869 A2 | 10/2006 |
| WO | 2006119085 A2 | 11/2006 |

OTHER PUBLICATIONS

Lucas, A. J., et al.; Development of a combined microPET-MR system; 2006; IEEE Nuclear Science Symposium Conf. Record; 4:2345-2348.

Schlyer, D., et al.; Development of a Simultaneous PET/MRI; 2004; IEEE Nuclear Science Symposium Conf. Record; 4:16-22.

Shaw, N. R., et al.; Genetic Algorithms for MRI Magnet Design; 2002; IEEE Trans. on Applied Superconductivity; 12 (1)733-736.

* cited by examiner

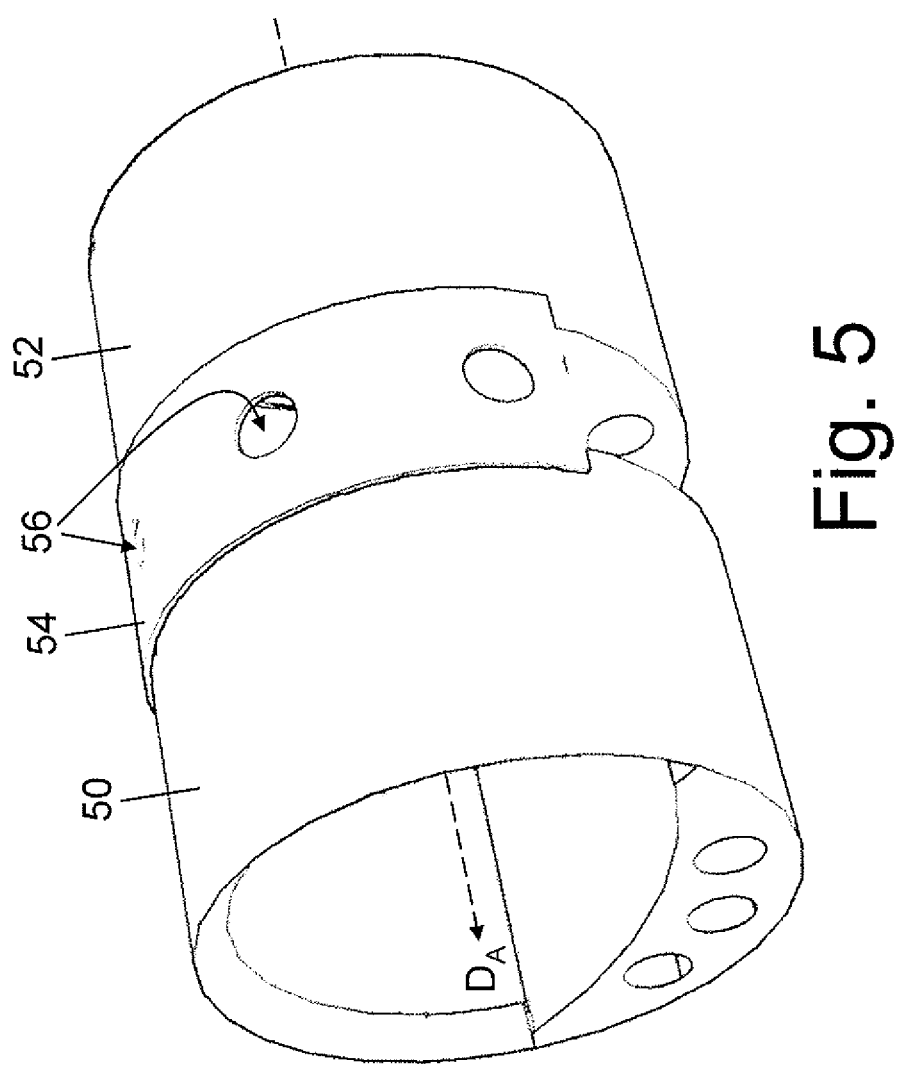

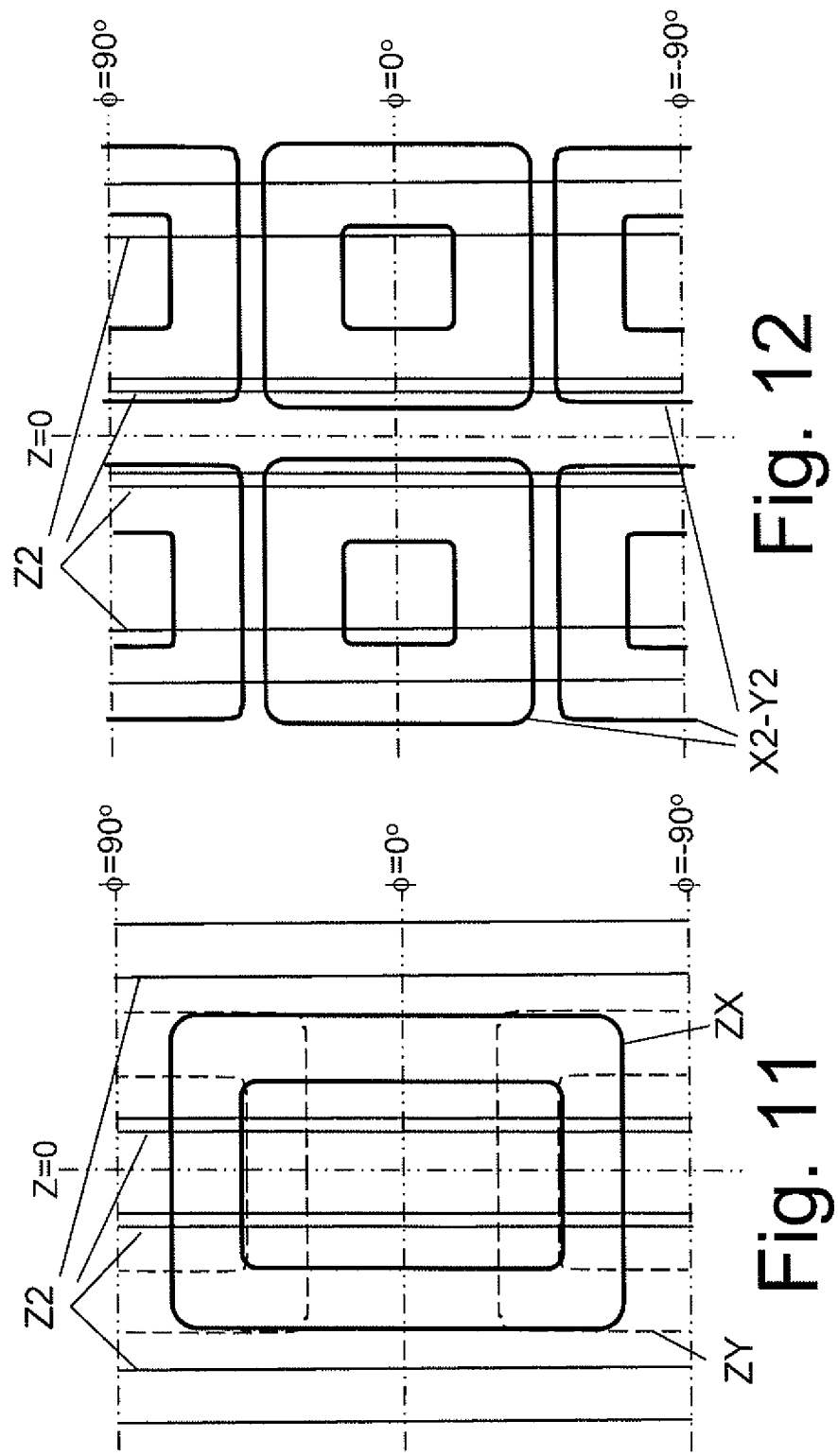

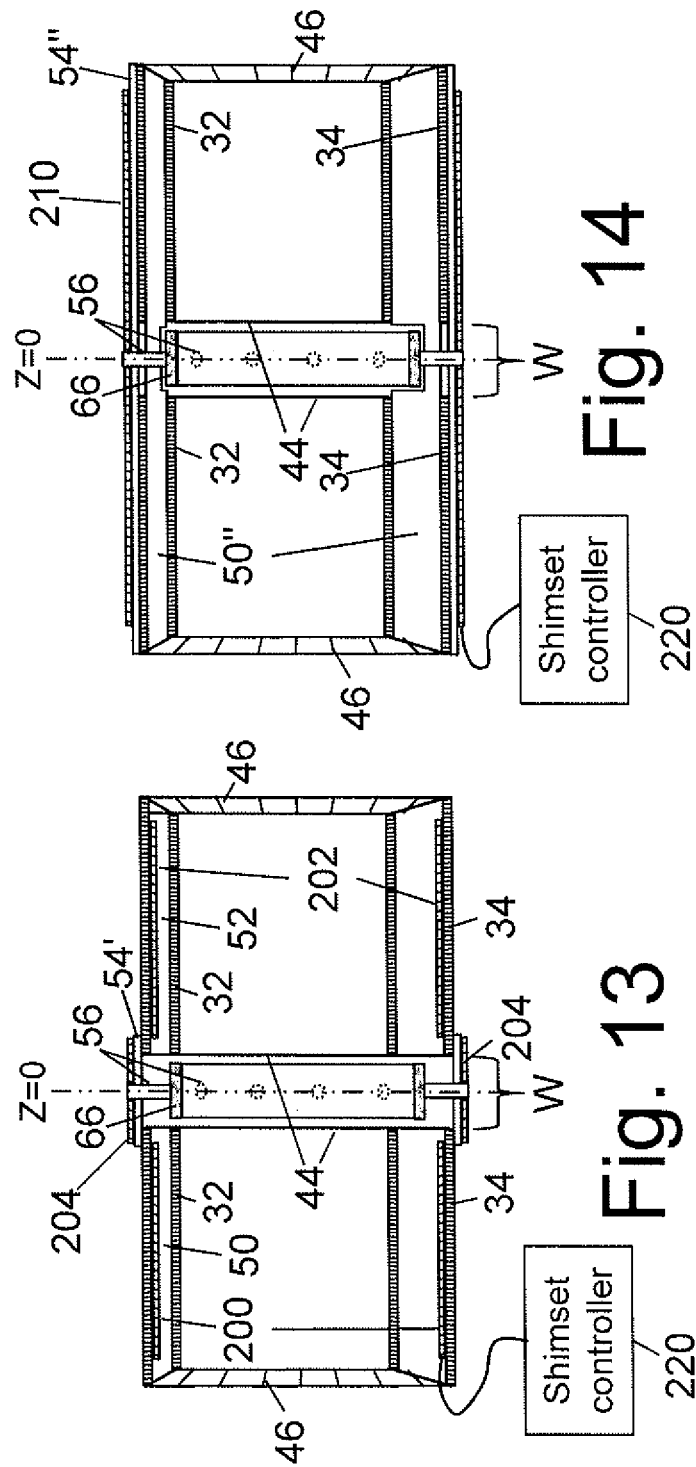

SPLIT GRADIENT COIL AND PET/MTI HYBRID SYSTEM USING THE SAME

CROSS REFERENCE TO RELATED APPLICATIONS

This application is a divisional application of U.S. patent application Ser. No. 12/531,979 filed Sep. 18, 2009 and since issued as U.S. Pat. No. 8,334,697 issued Dec. 18, 2012, which is a 371 application of PCT application number PCT/IB2008/050151 filed Jan. 16, 2008 which claims the benefit of U.S. provisional application Ser. No. 60/910,032 filed Apr. 4, 2007, all of which are incorporated herein by reference

DESCRIPTION

The following relates to the imaging arts. The following finds illustrative application to hybrid magnetic resonance scanning and positron emission tomography (PET) systems, and is described with particular reference thereto. The following finds more general application to magnetic resonance scanning systems with or without integrated radiation detectors for PET imaging.

Some existing magnetic resonance scanners include a generally cylindrical set of main magnetic field windings generating a main ($B_0$) magnetic field in at least an examination region disposed within the cylinder defined by the main magnet windings. A generally cylindrical gradient coil assembly is disposed coaxially inside the main magnetic field windings to selectively superimpose magnetic field gradients on a main magnetic field. One or more radio frequency coils are disposed inside the gradient coil assembly. These radio frequency coils can take various forms ranging in complexity from single-loop surface coils to complex birdcage coils. In some embodiments, a whole-body birdcage coil is provided, which is a cylindrical coil arranged coaxially inside of the gradient coil assembly. The gradient coil assembly and the radio frequency coil assembly are both whole-body cylindrical structures that are disposed at different radial positions, and as such they occupy a substantial amount of the cylindrical bore space.

Heid et al., U.S. Pat. No. 6,930,482, discloses a gradient coil having two separate halves that are separated by a central gap over which no windings pass. A short co-radial radio frequency coil is placed in the central gap so that the gradient coil and radio frequency coil are at about the same radius, thus making more efficient use of the valuable bore space. However, the efficiency of the gradient coil assembly decreases as the width of the central gap increases. For a central gap of more than about 10 centimeters, there is a substantial degradation of efficiency. The small achievable gap provides correspondingly short radio frequency coil rods or rungs, which reduces the field of view of the radio frequency coil.

There is also interest in multi-modality or hybrid scanners including both magnetic resonance and positron emission tomography (PET) capability. For example, Fiedler et al., WO 2006/111869 discloses various hybrid imaging systems. In some hybrid system embodiments disclosed in that reference, solid state PET detector elements are disposed between rungs of a whole-body birdcage coil in order to efficiently use the available cylindrical bore space. The gradient coil assembly of Heid et al., with its central gap, might also be considered as a promising candidate for use in a hybrid imaging system. However, the small central gap achievable using the gradient coil assembly of Heid et al. is likely to be too small to receive a practical assembly of PET detector elements. The usable portion of this already small gap is further reduced by spacing gaps that would be needed between the coil and the PET detectors to accommodate mechanical movement of the halves of the coil under the influence of Lorentz forces.

The following provides a new and improved apparatuses and methods which overcome the above-referenced problems and others.

In accordance with one aspect, a magnetic field gradient coil is disclosed, comprising a generally cylindrical set of coil windings defining an axial direction and including primary coil windings and shield coil windings at a larger radial position than the primary coil windings, the generally cylindrical set of coil windings having an arcuate or annular central gap that is free of coil windings, the central gap having an axial extent of at least ten centimeters and spanning at least a 180° angular interval, the generally cylindrical set of coil windings further including connecting conductors disposed at each edge of the central gap that electrically connect selected primary and secondary coil windings, the generally cylindrical set of coil windings being operable to superimpose a transverse magnetic field gradient on an axially oriented static magnetic field in a region of interest that is surrounded by the generally cylindrical set of coil windings responsive to electrical energizing of the generally cylindrical set of coil windings.

In accordance with another aspect, a magnetic resonance scanner is disclosed, comprising: a generally cylindrical set of coil windings defining an axial direction and including primary coil windings and shield coil windings at a larger radial position than the primary coil windings, the generally cylindrical set of coil windings having an arcuate or annular central gap that is free of coil windings, the central gap having an axial extent of at least ten centimeters and spanning at least a 180° angular interval, the generally cylindrical set of coil windings further including connecting conductors disposed at each edge of the central gap that electrically connect selected primary and secondary coil windings; and a main magnet disposed outside of the generally cylindrical set of coil windings and operable to generate an axially oriented static magnetic field in a region of interest surrounded by the generally cylindrical set of coil windings, the generally cylindrical set of coil windings being operable to superimpose a transverse magnetic field gradient on the axially oriented static magnetic field in the region of interest.

In accordance with another aspect, a magnetic resonance scanner is disclosed, comprising: an annular ring of positron emission tomography (PET) detectors; a generally cylindrical set of coil windings including primary coil windings and shield coil windings at a larger radius than the primary coil windings, the generally cylindrical set of coil windings having an annular central gap receiving the annular ring of PET detectors, the generally cylindrical set of coil windings further including connecting conductors disposed at each edge of the annular central gap that electrically connect selected primary and secondary coil windings; and a main magnet disposed outside of the generally cylindrical set of coil windings and operable to generate an axially oriented static magnetic field in a region of interest surrounded by the generally cylindrical set of coil windings, the generally cylindrical set of coil windings being operable to superimpose a transverse magnetic field gradient on the axially oriented static magnetic field in the region of interest.

In accordance with another aspect, a magnetic field gradient coil is disclosed, comprising: a generally cylindrical set of coil windings including primary coil windings and shield coil windings at a larger radial position than the primary coil windings; and a second order shimset comprising second order shim windings at least a portion of which are disposed at a larger radial position than the shield coil windings.

In accordance with another aspect, a hybrid scanner is disclosed, comprising: a magnetic resonance scanner; positron emission tomography (PET) detectors disposed proximate to an isocenter of the magnetic resonance scanner; and an active shim system including shim coils and a shimset controller configured to control the shim coils to compensate a magnetic field inhomogeneity induced by the PET detectors. In some embodiments, the shimset controller is configured to control the shim coils to apply a first correction when the PET detectors are operational and to apply a second correction different from the first correction when the PET detectors are non-operational.

One advantage resides in providing a magnetic field gradient coil with an arcuate or annular gap having a width that is larger than heretofore achievable.

Another advantage resides in providing a magnetic field gradient coil having a central gap of a width sufficient to receive a PET detector array.

Another advantage resides in providing a magnetic field gradient coil having an arcuate gap comporting with an asymmetrical radio frequency coil.

Another advantage resides in providing a hybrid magnetic resonance/PET scanner having improved vibrational isolation for the PET detectors.

Still further advantages of the present invention will be appreciated to those of ordinary skill in the art upon reading and understand the following detailed description.

Figure 2:
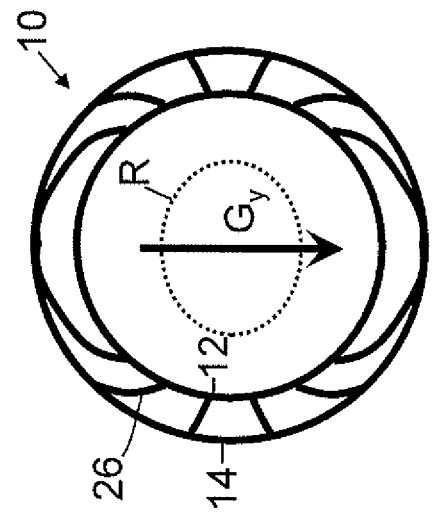

FIGS. 1 and 2 diagrammatically show perspective and end views, respectively, of a first illustrative transverse magnetic field gradient coil.

Figure 4:
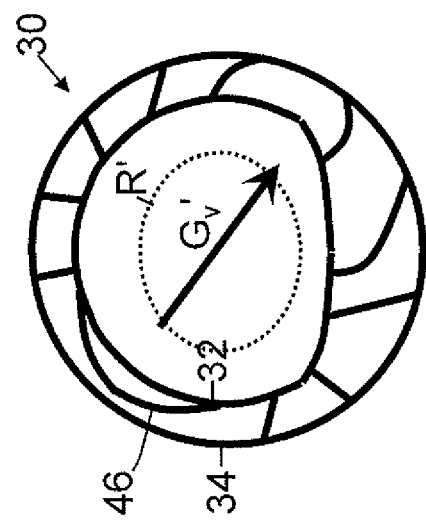
Figure 3:
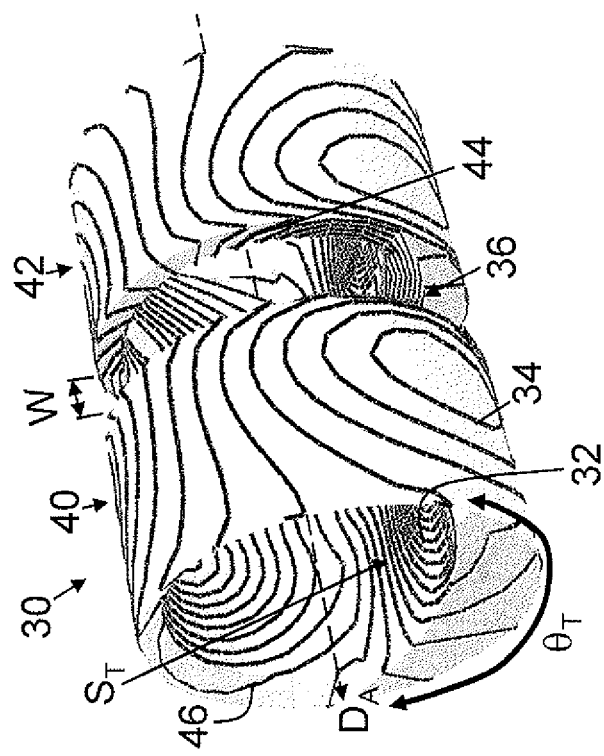

FIGS. 3 and 4 diagrammatically show perspective and end views, respectively, of a second illustrative transverse magnetic field gradient coil.

FIG. 5 diagrammatically shows a dielectric former for the second illustrative transverse magnetic field gradient coil including a stiffening brace.

Figure 6:
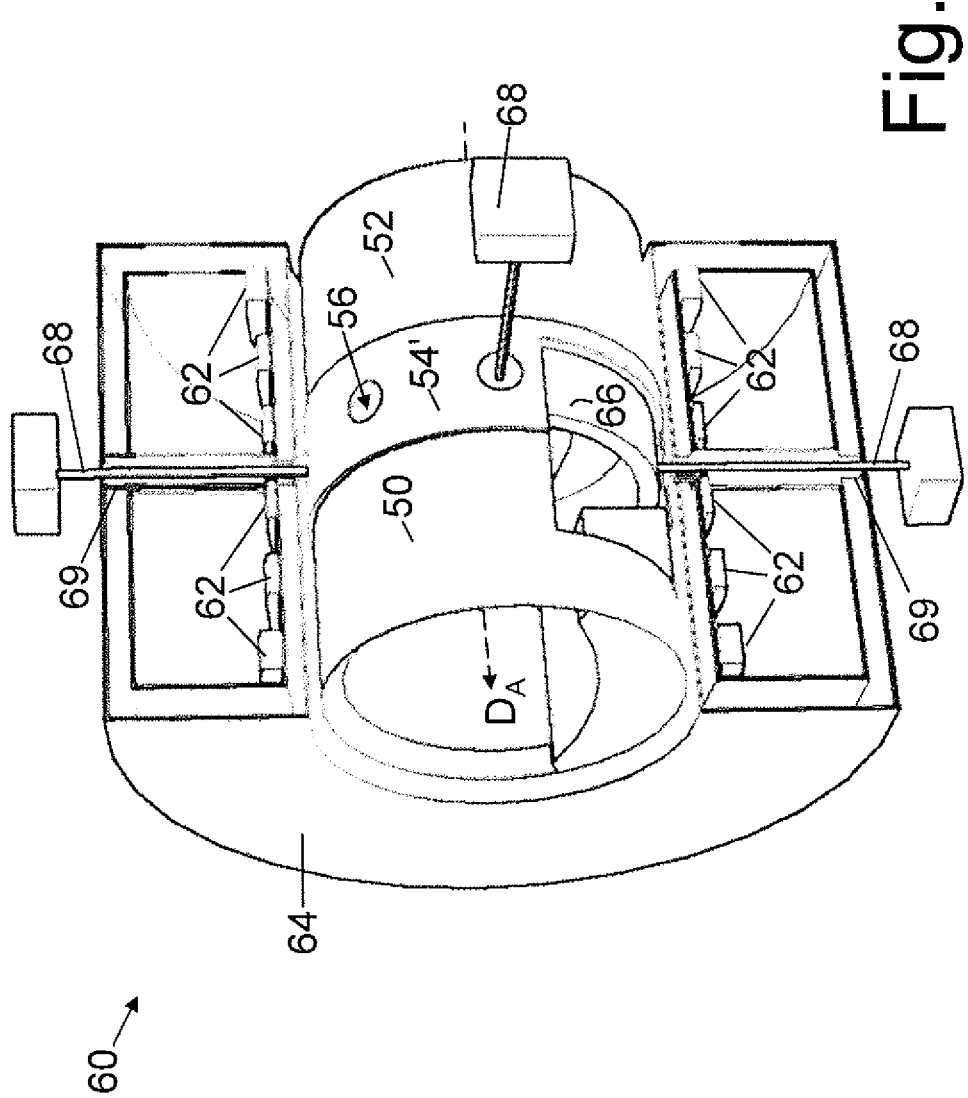

FIG. 6 diagrammatically shows a magnetic resonance scanner including the second illustrative transverse magnetic field gradient coil and an annular array of positron emission tomography (PET) detectors disposed in a central gap of the second illustrative transverse magnetic field gradient coil.

Figure 7:
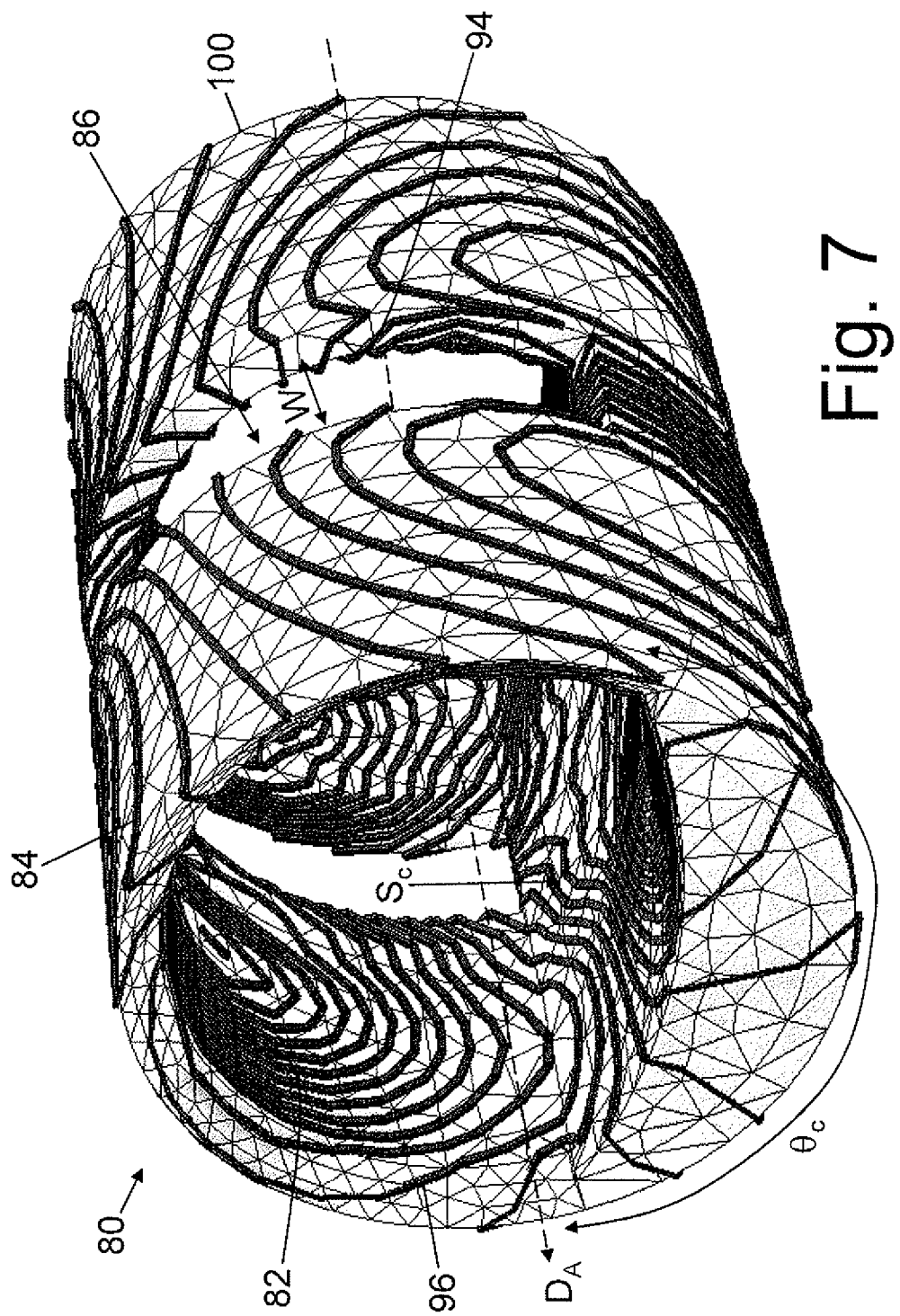

FIG. 7 diagrammatically shows a perspective view of a third illustrative transverse magnetic field gradient coil.

Figure 8:
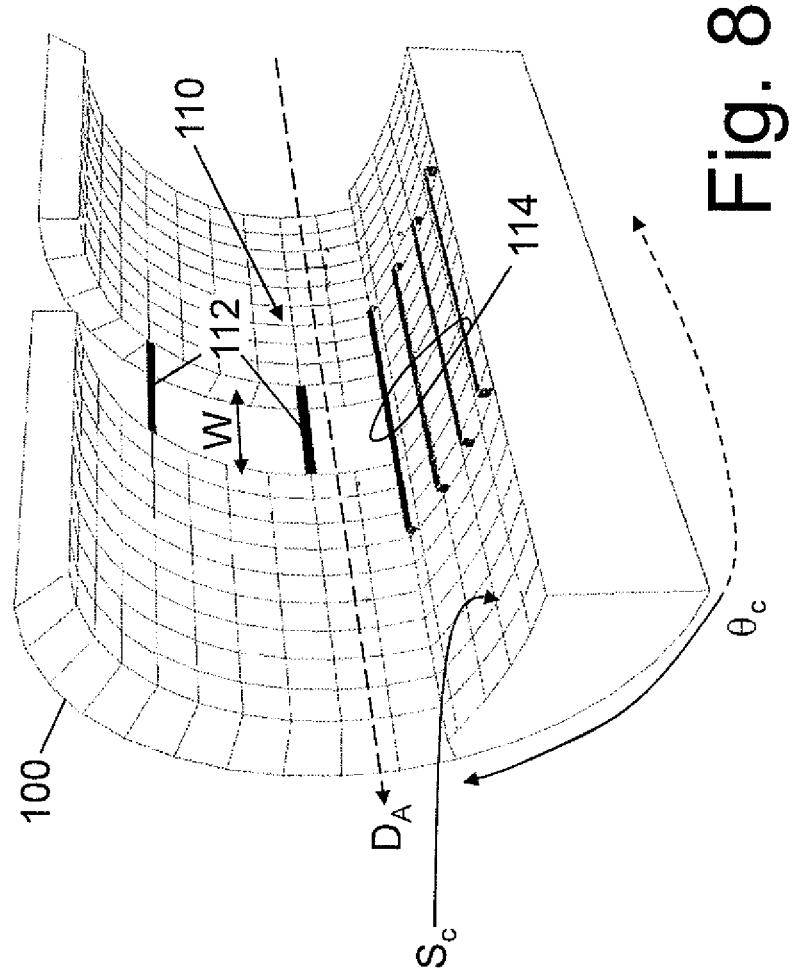

FIG. 8 diagrammatically shows a dielectric former for the third illustrative transverse magnetic field gradient coil along with annular conductors of a radio frequency coil.

Figure 9:
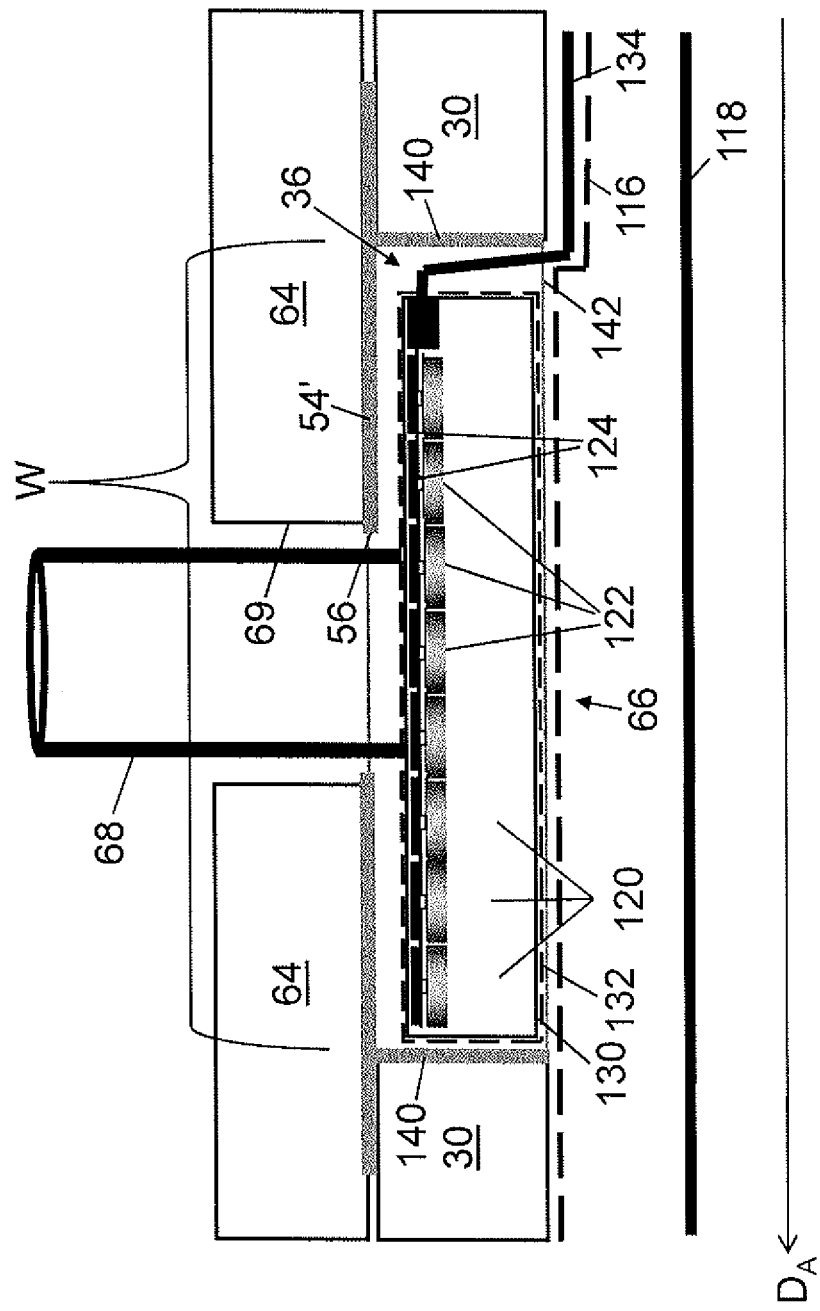

FIG. 9 diagrammatically shows a sectional view of a portion of a first embodiment of the annular array of PET detectors of FIG. 6.

Figure 10:
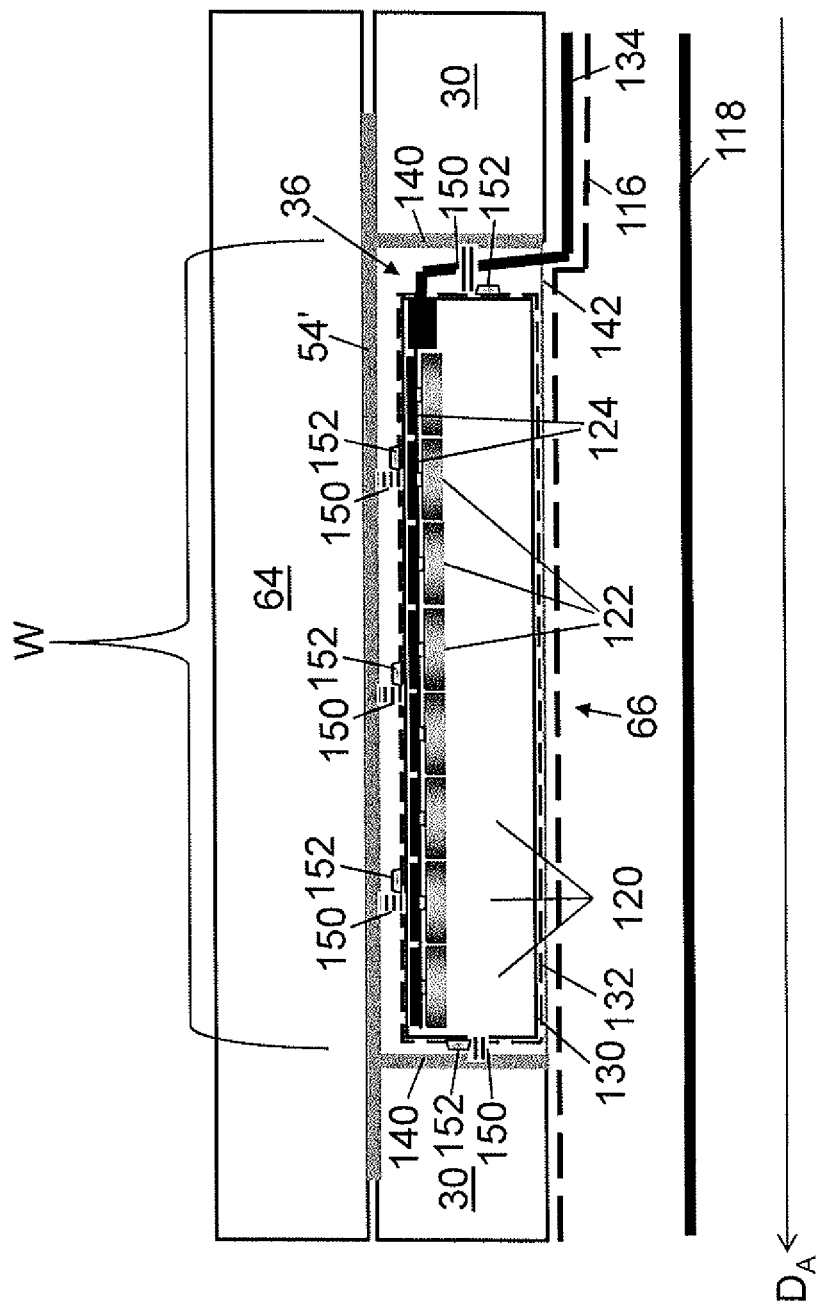

FIG. 10 diagrammatically shows a sectional view of a portion of a second embodiment of the annular array of PET detectors of FIG. 6.

FIGS. 11 and 12 plot selected Golay coil type shim coil patterns over ½ of the azimuthal range, that is, between azimuthal values between ɸ=−90° and ɸ=90°, with the azimuthal dimension unrolled to provide 2-D plots.

FIG. 13 plots a side sectional view of the gradient coil assembly of the hybrid PET/magnetic resonance scanner of FIG. 6 showing a suitable arrangement of second order shim coils on an outside of the split gradient coil and on a mechanical brace spanning the gradient coil portions.

FIG. 14 plots a side sectional view of the gradient coil assembly of a hybrid PET/magnetic resonance scanner showing a suitable arrangement of second order shim coils on an outer sheathing cylindrical former that also serves as structural reinforcement for the shim and gradient coils.

With reference to FIGS. 1 and 2, a magnetic field gradient coil includes a generally cylindrical set of coil windings 10 defining an axial direction $D_A$ (indicated by a dashed arrow in FIG. 1) and including primary coil windings 12 and shield coil windings 14 at a larger radial position than the primary coil windings. The generally cylindrical set of coil windings 10 has an arcuate or annular central gap 16 that is free of coil windings. The arcuate or annular central gap spans at least a 180° angular interval. In the embodiment shown in FIGS. 1 and 2 the central gap 16 is an annular gap that spans a full 360° so as to space apart two sub-sets 20, 22 of the generally cylindrical set of coil windings each including primary coil windings and shield coil windings at a larger radial position than the primary coil windings.

The generally cylindrical set of coil windings 10 further includes connecting conductors 24 disposed at each edge of the central gap 16 that electrically connect selected primary and secondary coil windings. The generally cylindrical set of coil windings 10 is operable to superimpose a transverse magnetic field gradient $G_y$ (indicated diagrammatically by an arrow in FIG. 2) on an axially oriented static magnetic field in a region of interest R (indicated diagrammatically by a dotted boundary line in FIG. 2, and axially centered on the central gap 16) that is surrounded by the generally cylindrical set of coil windings 10. The transverse magnetic field gradient $G_y$ is generated responsive to electrical energizing of the generally cylindrical set of coil windings 10. The embodiment of FIGS. 1 and 2 further includes connecting conductors 26 disposed at the ends of the coil windings 10 distal from the central gap 16. The connecting conductors 26 also electrically connect selected primary and secondary coil windings the selected windings being potentially the same as, or different from, the selected windings connected proximate to the central gap 16 by the connecting conductors 24. Moreover, some primary windings or secondary windings may be isolated windings that are not connected by any of the connecting conductors 24, 26. The connecting conductors 26 provide a relatively larger and more uniform field of view, as disclosed for example in Shvartsman et al., U.S. Publ. Appl. 2006/0033496 A1 which is incorporated herein by reference in its entirety.

The connecting conductors 24 enable non-zero current densities immediately adjacent the central gap 16 that compensate for the lack of any magnetically operative current density in the central gap 16. It is recognized herein that this compensation enables the central gap 16 to be made larger than would otherwise be possible while still maintaining acceptable coil efficiency and field quality. The central gap 16 has an axial extent W of at least ten centimeters, and more preferably at least about fifteen centimeters, and in some embodiments at least about twenty centimeters. Such a large central gap has various useful applications, such as providing space for transverse rungs or rods of a radio frequency coil, receiving components of a second imaging modality, or so forth.

The central gap 16 is free of coil windings, by which it is meant that there are no magnetically operative conductors disposed in the central gap 16. It is to be understood that one or more current feed conductors (not shown) optionally cross the central gap 16, for example to electrically connect the two sub-sets of conductors in series. Such current feed conductors, if included, are not magnetically operative conductors in that they are not designed to contribute in a substantial way, and do not contribute in a substantial way, to the magnetic field generated by the generally cylindrical set of coil windings 10.

The generally cylindrical set of coil windings 10 shown in FIGS. 1 and 2 is configured with the "fingerprints" of the primary and shield coil windings 12, 14 aligned vertically. This generates the transverse magnetic field gradient $G_y$ along the vertical direction, corresponding to the conventional "y" coordinate of a typical magnetic resonance scanner. In a typical arrangement, a corresponding set of windings rotated 90° respective to the illustrated generally cylindrical set of coil windings 10 is provided to selectively generate a magnetic field gradient along an "x" direction transverse to the "y" direction. It will be noted that the generally cylindrical set of coil windings 10 is rotatable such that the illustrated magnetic field gradient can be aligned with the "y" direction as shown, or with the aforementioned "x" direction, or with any other direction transverse to the axial direction. The illustrated alignment along the "y" direction, or along the "x" direction as suggested here, is convenient in that it matches conventional Cartesian x-y-z coordinates sometimes used in magnetic resonance imaging; however, the generally cylindrical set of coil windings 10 can have any orientation.

The precise configuration of the generally cylindrical set of coil windings 10 is designed to provide good magnetic field gradient uniformity at least across the region R of interest. Such design is suitably performed using a stream function approach, as described for example in Peeren, "Stream Function Approach for Determining Optimal Surface Currents", Journal of Computational Physics vol. 191 pages 305-21 (2003) and in "Stream Function Approach for Determining Optimal Surface Currents", Doctoral Thesis of Gerardus N. Peeren (Eindhoven University of Technology 2003), both of which are incorporated herein by reference in their entirety. The stream function approach determines a continuous current density distribution, represented by a stream function, that provides a specified magnetic field distribution, and then discretizes the obtained stream function to obtain the coil windings distribution.

With reference to FIGS. 3 and 4, a second magnetic field gradient coil embodiment is similar to the coil embodiment of FIGS. 1 and 2, and includes a generally cylindrical set of coil windings 30 defining the axial direction $D_A$ and including primary coil windings 32 and shield coil windings 34 at a larger radial position than the primary coil windings. The generally cylindrical set of coil windings has an arcuate or annular central gap 36 that is free of coil windings. The arcuate or annular central gap spans at least a 180° angular interval. In the embodiment shown in FIGS. 3 and 4 the central gap 36 is an annular gap that spans a full 360° so as to space apart two sub-sets 40, 42 of the generally cylindrical set of coil windings 30 each including primary coil windings and shield coil windings at a larger radial position than the primary coil windings. The generally cylindrical set of coil windings 30 includes connecting conductors 44 disposed at each edge of the central gap 36 that electrically connect selected primary and secondary coil windings. The embodiment of FIGS. 3 and 4 further includes connecting conductors 46 disposed at the ends of the coil windings 30 distal from the central gap 36. The connecting conductors 46 also electrically connect selected primary and secondary coil windings the selected windings being potentially the same as, or different from, the selected windings connected proximate to the central gap 36 by the connecting conductors 44. Moreover, some primary windings or secondary windings may be isolated windings that are not connected by any of the connecting conductors 44, 46.

The primary coil windings 32 of the generally cylindrical set of coil windings 30 are disposed at a non-constant smaller radial position over a selected angular interval $\theta_T$ to define an approximately planar surface $S_T$. While the surface $S_T$ is approximately planar, it may have some bowing or curvature as shown in FIG. 3. The effect is that the primary coils in the selected angular interval $\theta_T$ are moved upward to be closer to the subject. For spine imaging, for example, this closer positioning of the primary coils in the selected angular interval $\theta_T$ enhances radio frequency coupling with the spine when the subject lies on a generally planar subject support overlaying the primary coils in the selected angular interval $\theta_T$.

The generally cylindrical set of coil windings 30 of FIGS. 3 and 4 is configured with the "fingerprints" of the primary and shield coil windings 32, 34 rotated by about 45° away from the vertical. This generates a transverse magnetic field gradient $G_y'$ oriented at about a 45° angle respective to the vertical. The windings are designed using the stream function approach so that the transverse magnetic field gradient $G_y'$ is substantially uniform at least within a region R' of interest. Using this approach with the illustrated 45° rotation of the gradient field, a transverse gradient coil was designed to have the annular central gap 36 with width W of twenty centimeters.

With reference to FIG. 5, the two sub-sets 40, 42 of the generally cylindrical set of coil windings 30 are suitably supported by or in two respective dielectric formers 50, 52 that are spaced apart by about the gap width W. The two sub-sets 40, 42 of the gradient coil assembly 30 and their respective carriers 50, 52 are prone to mechanical canting caused by substantial Lorentz forces generated during operation of the generally cylindrical set of coil windings 30. To combat this, a stiffening brace 54 optionally spans the annular central gap 36 to substantially rigidly connect the two spaced apart generally cylindrical dielectric formers 50, 52. In the embodiment of FIG. 5, the brace 54 is arcuate and spans about 180°. In other embodiments, a complete annular brace is contemplated. In some embodiments to be described, components such as a radio frequency coil, an array of positron emission tomography (PET) detectors, or so forth are contemplated to be disposed in the central gap 36. In some such embodiments, the optional brace 54 may include openings 56 providing pass-throughs for mounting members that provide independent support for such components.

With reference to FIG. 6, for example, the dielectric formers 50, 52 are disposed in a magnetic resonance scanner 60 that includes main magnet windings 62 disposed in a cryogenic housing 64 defining a main magnet producing the static axially oriented $B_0$ magnetic field in the region R' of interest. An annular ring of positron emission tomography (PET) detectors 66 are disposed in the annular central gap 36 of the generally cylindrical set of coil windings 30, that is, in the gap between the dielectric formers 50, 52 that support the coil windings 30. A brace 54', which in this embodiment is an annular brace, lies outside the dielectric formers 50, 52 and outside the annular ring of PET detectors 66. Independently supported mounting members 68 pass through the openings 56 in the brace 54' and openings 69 in the magnet housing 64 to support the annular ring of PET detectors 66 independently from the dielectric formers 50, 52 supporting the generally cylindrical set of coil windings 30 (not shown in FIG. 6). Such independent support is advantageous because the gradient coils move and accelerate during operation due to Lorentz forces, and such movement, if transferred to the PET detectors 66, would result in degradation of PET images acquired using the PET detectors 66. In some embodiments, the dielectric formers 50, 52 and the brace 54' define a stiff unit that is vibrationally isolated from the annular ring of PET detectors 66 and the mounting members 68. In one suitable approach, the stiff unit 50, 52, 54' is mounted to the magnet housing 64 which in turn is mounted to a floor of a room. The mounting members 68 are independently mounted to the floor, walls, and ceiling of the room. This provides the desired vibrational isolation because the floor of the room is massive enough that it absorbs vibrations generated in the stiff unit 50, 52, 54' by the generally cylindrical set of coil windings 30 so that these vibrations are not transferred to the mounting members 68.

The outer support (not shown) to which the mounting members 68 connect can be a sub-frame completely surrounding the magnetic resonance scanner 60, a set of hard points on the walls of the room containing the scanner 60, or so forth. In order to enable the mounting members 68 to pass through the magnet housing 64 while enabling the housing 64 to maintain vacuum and cryogenic reservoir integrity, the mounting members 68 suitably pass through openings 69 formed as tubular pass-through regions whose ends are sealed to maintain vacuum and helium can integrity. Optionally, a radio frequency screen (not shown in FIG. 6) can extend into the openings 69 to provide RF isolation. Additional pass-through openings can be provided for electrical and other connections to the annular ring of PET detectors 66. As the pass-through openings are relatively small, they can be interspersed amongst the main magnet windings 62 so that the magnetic design of the main magnet is substantially unaffected.

The generally cylindrical sets of coil windings 10, 30 have complete annular gaps 16, 36 which advantageously can receive an annular component such as the annular array of PET detectors 66 as shown in FIG. 6. Having the illustrated complete annular array of PET detectors 66 provides better image resolution and image quality as compared with a less complete array of PET detectors, such as an arcuate array that spans less than a complete 360°. However, better magnetic gradient uniformity and coil efficiency can be achieved by having an arcuate gap that does not extend the full 360°.

With reference to FIG. 7, a third magnetic field gradient coil embodiment is similar to the second gradient coil embodiment of FIGS. 3 and 4, and includes a generally cylindrical set of coil windings 80 defining the axial direction $D_A$ including primary coil windings 82 and shield coil windings 84 at a larger radial position than the primary coil windings. The generally cylindrical set of coil windings has an arcuate or annular central gap 86 that is free of coil windings. The arcuate or annular central gap spans at least a 180° angular interval. In the embodiment shown in FIG. 7 the central gap 86 is an arcuate gap of axial extent W that spans an angular interval of greater than 180° but less than 360°, there being coil windings disposed over the complementary angular interval $\theta_c$ not spanned by the central gap 86. The generally cylindrical set of coil windings 80 includes connecting conductors 94 disposed at each edge of the central gap 86 that electrically connect selected primary and secondary coil windings. The embodiment of FIG. 7 further includes connecting conductors 96 disposed at the ends of the coil windings 80 distal from the central gap 86. The connecting conductors 96 also electrically connect selected primary and secondary coil windings the selected windings being potentially the same as, or different from, the selected windings connected proximate to the central gap 86 by the connecting conductors 94. Moreover, some primary windings or secondary windings may be isolated windings that are not connected by any of the connecting conductors 94, 96.

The primary coil windings 82 of the generally cylindrical set of coil windings 80 are disposed at a non-constant smaller radial position over the complementary angular interval $\theta_c$ to define an approximately planar surface $S_c$. While the surface $S_c$ is approximately planar, it may have some bowing or curvature as shown in FIG. 7. The effect is that the primary coils in the selected angular interval $\theta_c$ are moved upward to be closer to the subject. For spine imaging, for example, this closer positioning of the primary coils in the complementary angular interval $\theta_c$ enhances radio frequency coupling with the spine when the subject lies on a generally planar subject support (not shown) overlaying the primary coils in the complementary angular interval $\theta_c$. The arcuate gap 86 is advantageous for spine imaging because it does not extend under the spine—rather, gradient coil windings of the primary and shield coil windings 82, 84 are continuous under the spine for typical spinal imaging arrangements in which the subject lies supine during the spinal imaging. In FIG. 7, a dielectric former 100 supporting the coil windings 82, 84 is shown in a wire frame representation.

Preliminary calculations for a coil configured in accordance with the design of FIG. 7 have shown that for a gradient gap width W of twenty centimeters in the upper region and a gradient bore size of seventy-two centimeters, a stored energy of less than 4.4 J can be expected at 10 mT/m. In this coil design, the zero-level of the magnetic field gradient is vertically offset from the mechanical z-axis or isocenter of the surrounding cylindrical ($B_0$) magnet by about 10-15 centimeters. This offset is recognized herein as improving the efficiency of the gradient coil. In contrast, if the zero-level of the magnetic field gradient precisely coincides with the mechanical z-axis or isocenter of the cylindrical ($B_0$) magnet, then relatively more windings are included in the upper part of the coil and fewer in the complementary angle interval $\theta_c$, but overall more ampere-turns are included and the stored energy is higher. These considerations also apply to the design of the generally cylindrical set of coil windings 30 in which the central gap 36 is annular.

The illustrated arcuate gap 86 has a constant width W (except over the complementary angular interval $\theta_c$ where the gap is absent). However, it is contemplated for the width of the gap to vary with angular position to trade off between magnetic field gradient performance of the magnetic field gradient coil (improved by having a smaller gap) and RF performance of the radio frequency coil (improved by having a larger gap and concomitantly axially longer upper conductors).

With continuing reference to FIG. 7 and with further reference to FIG. 8, a further advantage of the arcuate gap 86 is that it comports with a radio frequency coil 110 that is designed for spine imaging. In FIG. 8, the dielectric former 100 is shown, along with axially oriented conductors of the radio frequency coil 110. To conserve bore space, upper axially oriented conductors 112 are disposed in the arcuate central gap 86 and are substantially axially coextensive with the axial extent W of the arcuate central gap 86. This arrangement efficiently uses the available bore space by placing the coil windings 82, 84 and the upper axially oriented conductors 112 at about the same radial position. Moreover, the upper axially oriented conductors 112 are located relatively far away from the spine, that is, relatively far away from the region of interest for spinal imaging. On the other hand, lower axially oriented conductors 114 are positioned in the region of the complementary angular interval $\theta_c$ where the primary coil windings 82 are raised to conform with a generally planar subject support (not shown). In this region, the lower axially oriented conductors 114 are positioned above the primary coil windings 82 and are substantially longer than the axial extent W of the central gap 86. The longer lower axially oriented conductors 114 advantageously provide a larger and more uniform field of view of the proximate spinal region of interest. In some contemplated embodiments, the lower axially oriented conductors 114 of the radio frequency coil 110 are configured as a SENSE-capable receive array. For this purpose, the lower axially oriented conductors 114 can optionally be segmented along the axial direction. Such a configuration is suitably operated using multi-point excitation, for example by a power splitter or with multiple power amplifiers.

With returning reference to FIG. 6 and with further reference to FIG. 9, a suitable embodiment of the annular ring of PET detectors 66 is further described. FIG. 9 shows a sectional view of a portion of the PET detectors 66 disposed in the central gap 36 of the generally cylindrical sets of coil windings 30, between the inner surface of the cylindrical magnet housing 64 and a radio frequency screen 116 of an optional birdcage-type radio frequency coil (a rung 118 of which is visible in the diagrammatic sectional view of FIG. 9). At least in the area of the PET detectors 66, the radio frequency coil components 118 are made of thin copper strips without capacitors to reduce the scattering of gamma particles. For example, copper strips of thickness five or six times greater than the RF skin depth (e.g., about six microns for $^1$H magnetic resonance in a 3-Tesla scanner) are suitable. The radio frequency screen 116 is similarly made of a thin conductive foil or mesh that is substantially transparent to gamma particles.

The PET detectors 66 include an array of scintillators 120 that are viewed by an array of photodetectors 122. In some embodiments, the photodetectors 122 are silicon photomultipliers (SiPM's). Some suitable SiPM devices are described in Frach et al., WO 2006/111883 A2 and in Fiedler et al., WO 2006/111869 A2, both of which are incorporated herein by reference in their entireties. The photodetectors 122 are electrically connected with time domain conversion (TDC)/analog-to-digital conversion (ADC) electronics 124 that convert radiation detection events into digital data including digitized intensity information corresponding to the detected particle energy and a digital timestamp indicating the detection time. In some embodiments, SiPM detectors 122 and TDC/ADC electronics 124 are monolithically integrated on common silicon substrates. In some other embodiments, some or all of the TDC and/or ADC processing is disposed remotely away from the scanner. In yet other contemplated embodiments, the annular ring of PET detectors disposed in the gap 36 includes only the scintillators 120 and coupled optical fibers that transmit scintillation light off of the scanner to remotely located photodetectors and associated remotely located TDC/ADC electronics.

The radiation detection hardware 120, 122, 124 is disposed in light shielding 130 (indicated by a solid line) to avoid spurious detection of light photons, and inside of a galvanic isolation container 132 (indicated by a dashed line) such as a radio frequency screen to suppress radio frequency interference. The galvanic isolation container 132 provides broadband RF shielding, whereas the radio frequency screen 116 is a low pass filter that provides RF shielding at the magnetic resonance frequency and allows the pulsed magnetic field gradients to be substantially unaffected by the RF shielding. Power and communication cabling 134 is suitably run outside of the radio frequency screen 116 to keep these cables outside of the high RF field.

To suppress interaction of the PET detectors 66 with the magnetic field gradients, the stiff brace 54' that secures the generally cylindrical set of coil windings 30 also defines a thick copper shield 54'. This shield 54' is mechanically connected with the magnet housing 64, and includes extensions 140 into the central gap 36 of the generally cylindrical set of coil windings 30 to enhance shielding of the PET detectors 66 against the generated magnetic field gradients. The thick copper shield 54' is either left open in front of the PET detectors 66 to avoid blocking gamma particles, or includes a thinned front portion 142 that is substantially transmissive to gamma particles. The various shielding components can be variously combined—for example, it is contemplated in some embodiments to integrate the thinned front portion 142 of the gradient shield with the galvanic isolation container 132. Moreover, selected shielding components are optionally omitted (possibly at the cost of higher interaction between the magnetic resonance and PET components). As noted previously with reference to FIG. 6, the mounting members 68 pass through openings 69 in the magnet housing 64 and openings 56 in the shielding and mechanical bracing component 54' to independently support the PET detectors 66.

With reference to FIG. 10, in an alternative embodiment vibrational isolation of the PET detectors 66 is achieved by using compensatory piezo-actuators 150 disposed between the annular ring of PET detectors 66 and the support (e.g., the dielectric formers 50, 52 and the stiff brace 54') of the generally cylindrical set of coil windings 30 to support the PET detectors 66 while vibrationally isolating the PET detectors 66 from the generally cylindrical set of coil windings 30. The piezo-actuators 150 are operatively coupled with acceleration sensors 152, such as MEMS-based accelerometers, and are configured in a feedback loop to adjust the piezo-actuators 150 to minimize acceleration of the PET detectors 66 as indicated by the acceleration sensors 152. In some embodiments, the piezo-actuators 150 and the acceleration sensors 152 are monolithically integrated as a single unit, for example formed into or on a silicon substrate. Because the acceleration levels are large but the displacements are of order a few millimeters or less, tolerances of a as small as a few microns between edges of the central gap 36 and the PET detectors 66 are contemplated. In some embodiments, it is contemplated to include openings in the containment formed by the brace 54' and the walls of the central gap 36 to provide fluid communication to avoid air compression during rapid acceleration. Additionally or alternatively, larger tolerances can be used to provide air cushioning. The array of piezo-actuators 150 preferably provides acceleration suppression along three displacement degrees of freedom (e.g., along the three orthogonal coordinates of a Cartesian system) and three rotational degrees of freedom. Advantageously, by using the piezo-actuators 150 or vibration isolation it is possible to eliminate the independent mounting members 68 and corresponding openings 56, 69 in the stiff brace 54' and magnet housing 64.

The scanner of FIG. 6 is suitably operated as a hybrid scanner. Because the annular array of PET detectors 66 is disposed in the central gap 36 of the generally cylindrical magnetic field gradient windings 30, the field-of-view (FOV) for PET imaging is substantially centered at the same position as the FOV for magnetic resonance imaging, although some PET/MR FOV offset in the axial direction and/or transverse to the axial direction is contemplated. The FOV for PET imaging can be the larger, smaller, or the same size as the FOV for magnetic resonance imaging. In some approaches, magnetic resonance and PET imaging are done in succession, or PET and magnetic resonance imaging periods are interleaved in time. In other embodiments, it is contemplated to perform PET imaging and magnetic resonance imaging simultaneously.

In the illustrated embodiments, the annular ring of PET detectors 66 advantageously provides a full 360° angular coverage for data collection. As is known in the art, less than full 360° coverage tends to lead to image artifacts resulting from missing lines of response due to the missing angular span of detectors. However, it is contemplated to use an arcuate set of PET detectors that spans at least a 180° angular interval but less than a full 360°. For example, such an arcuate set of PET detectors may be inserted into the arcuate gap 86 of the generally cylindrical sets of coil windings 80. The missing lines of response can be compensated by acquiring additional information via time-of-flight localization along the lines of response. Other configurations of PET detectors are also contemplated, such as a plurality of interrupted angular spans of PET detectors that collectively provide at least 180° of angular coverage.

In some embodiments, it may be desired to include shim coils for correcting the magnetic field gradients for loading effects on the static ($B_0$) magnetic field. While first order magnetic field shims are advantageous, second order shim sets provide more control for shimming the ($B_0$) magnetic field. In hybrid embodiments, the annular ring of PET detectors 66 has the potential to produce further magnetic field inhomogeneity which may also be correctable using second order active coil shim sets.

With reference to FIGS. 11 and 12, some second order shim coils include portions passing through the scanner center (that is, the shim coils cross the axial plane denoted z=0 in FIGS. 11 and 12). FIGS. 11 and 12 plot selected Golay coil type shim coil patterns over ½ of the azimuthal range, that is, between azimuthal values between $\phi=-90°$ and $\phi=90°$, with the azimuthal dimension unrolled to provide 2-D plots. For example, FIG. 11 plots Golay coil type shim sets for the zx second order shim coil set ZX and for the $z^2$ second order shim coil set Z2. The ZY second order shim coil set ZY is also indicated in dashed lines, and is identical to the ZX second order shim set ZX except that it is rotated 90° in the azimuthal ($\phi$) direction. FIG. 12 plots the $z^2$ second order shim coil set Z2 and also the ($X^2-Y^2$) second order shim coil set X2-Y2. It will be noted that the ($X^2-Y^2$) and $Z^2$ second order shim sets have a central gap at Z=0; accordingly, these shim coils could conceivably be mounted on the dielectric former portions 50, 52 of FIG. 6 as long as the central gap is small enough. However, the ZX and ZY second order shim sets have no central gap and are centered on and cross the z=0 plane. Accordingly, the ZX and ZY second order shim sets cannot be mounted on the dielectric former portions 50, 52.

FIG. 13 plots a side sectional view of the gradient coil assembly of the hybrid PET/magnetic resonance scanner of FIG. 6, showing one suitable arrangement of second order shim coils. In this embodiment the second order shim coils are divided into first and second groups 200, 202 that are disposed on or in the two dielectric former portions 50, 52, respectively, between the primary and shield gradient coil windings 32, 34. This arrangement is similar to that of second order shim coils in existing magnetic resonance scanners, in which the second order shim coils are disposed between the primary and shield gradient coil windings. To span the central gap, a central third group 204 of second order shim coil windings are disposed on the mechanical brace 54' that provides support for the dielectric former portions 50, 52 and maintains the spacing and relative positioning of the dielectric former portions 50, 52 in the presence of Lorentz forces induced by energizing of the gradient windings. The shim set 200, 202, 204 can be similar to a Golay coil type shimset for second order gradients. The shim coil conductors of the central group 204 are suitably locally perturbed or routed to avoid the openings 56 in the mechanical brace 54' that provide access for the mounting members 68 (shown in FIG. 6). Additionally or alternatively, the openings 56 can be located to avoid the shim conductors of the third shim coils group 204. The shimset in the embodiment illustrated in FIG. 13 has certain shim coils located between the primary and shield gradient coil windings 32, 34; alternatively portions of the shim windings may be disposed outside of the shield gradient coil windings 34.

The brace 54' overlaps the dielectric former portions 50, 52 in order to provide for a secure connection of the brace 54' to the former portions 50, 52. In some embodiments, this overlap and the axial extent W of the central gap is such that the ZX and ZY second order shimming windings can be disposed entirely in the central group 204, and the $Z^2$ and ($X^2-Y^2$) second order shim windings can be disposed entirely in the first and second groups 200, 202. In this case, the first and second groups 200, 202 and the third group 204 are advantageously operationally separate. On the other hand, in some embodiments the overlap of the brace 54' with the dielectric former portions 50, 52 may be too small, or the axial extent W of the central gap may be too wide, to enable such a convenient separation of the shim coil sets. In this latter case, jumper conductors (not shown) electrically connect windings of the first and second groups 200, 202 and the third group 204, for example to interconnect portions of a ZX shim coil residing in part on each of the three shimset groups 200, 202, 204. The difference in radial positions of the first and second groups 200, 202, on the one hand, and the central third group 204 on the other hand is relatively small (e.g., of order equal to the combined thicknesses of the shield gradient windings layer 34 and the thickness of the brace 54'), and so the electrical jumpers can be made relatively short. The shimset 200, 202, 204 is a three-dimensional shimset, and can be designed using stream function approaches as described in the Peeren references already cited and incorporated herein by reference.

As yet another approach (not illustrated herein), it is contemplated to design the second order shimset coils with the central gap (that is, with no windings extending into the axial extent W of the central gap) and to design the coils to provide the desired second order magnetic shimming fields using the stream function approach. If the axial extent W of the central gap is small enough, this approach is expected to be feasible even for ZX and ZY shim coils. By defining the ZX or ZY shim coil to include windings on two spaced apart radial surfaces connected at the edge of the central gap by connectors similar to the connectors 44 for the gradient windings, the ZX or ZY shimming current at the edge of the central gap can be made nonzero, thus providing flexibility in the stream line design optimization to compensate for the windings missing in the central gap.

FIG. 14 plots a side sectional view of the gradient coil assembly of the hybrid PET/magnetic resonance scanner of FIG. 6, modified in that the two dielectric former portions 50, 52 are replaced by a single cylindrical dielectric former 50" that supports the primary and shield gradient coil windings 32, 34 and has a central annular indentation or slot that receives the annular ring of PET detectors 66. In this arrangement the brace 54' can be omitted in its entirety. Alternatively, if the central annular indentation or slot receiving the PET detectors 66 makes the dielectric former 50" too mechanically weak, then a reinforcing outer cylindrical brace 54" can be disposed around the dielectric former 50". Second order shimset windings 210 can be disposed on the outer surface of the dielectric former 50" or on the outer surface of the optional reinforcing outer cylindrical brace 54". In this embodiment, standard Golay second order shim windings can be used, optionally with some rerouting or distortion of the windings in the vicinity of the openings 56 receiving the supports PET detectors ring 66.

With continuing reference to FIGS. 13 and 14, a shimset controller 220 applies electrical current to selected second order shims of the shimset to produce desired second order shimming. The shimsets 200, 202, 204, 210 can be configured and energized by the shimset controller 220 to correct for subject loading inhomogeneities, either in a static fashion or dynamically during magnetic resonance acquisition pulse sequences. Additionally, the shimsets 200, 202, 204, 210 can be configured and energized by the shimset controller 220 to correct for inhomogeneities introduced by the annular ring of PET detectors 66. These latter inhomogeneities may depend upon the operational state of the PET detectors. The nonoperational PET detectors can be expected to introduce some magnetic field inhomogeneities due to the presence of electrically conductive components in the PET detectors that may have a weak or residual effect on the static magnetic field. During PET acquisition, the operating PET detectors are electrically biased and electrical currents flow in the PET detectors and related circuitry. These operational aspects can introduce additional magnetic field inhomogeneities. Accordingly, in some embodiments the shimset controller 220 applies shim currents that are calibrated for the operational and nonoperational states of the PET detector ring 66, respectively, and the appropriate shim currents calibration is used during simultaneous MR/PET or MR-only imaging, respectively.

Further, the calibration examination volume may be differently selected for the operational and nonoperational states of the PET detector ring 66, respectively. For example, if the PET system has a smaller field of view than the magnetic resonance scanner, then the shims calibration for the simultaneous MR/PET operation may shim the magnetic field to be uniform within a smaller examination region sized to match the relatively small PET examination region. By calibrating the shimming for the smaller PET examination volume, improved magnetic field uniformity is expected to be achievable, albeit only in the PET examination region. This spatial limitation is acceptable for simultaneous PET/MR imaging, since typically only the region that is imaged by both PET and MR is of interest in this case. On the other hand, during MR-only operation it may be advantageous for the MR-only shims calibration to shim the entire larger magnetic resonance examination volume.

The illustrated shimsets 200, 202, 204, 210 are configured to comport with the split gradient coil in which the central gap is an annular gap completely dividing the gradient windings into two separate sections. However, the illustrated shimsets are readily adapted for use in conjunction with a coil such as that shown in FIG. 7 in which the central gap is an arcuate but not a complete annular gap.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A magnetic resonance scanner comprising:
    a generally cylindrical set of coil windings defining an axial direction and including primary coil windings and shield coil windings at a larger radial position than the primary coil windings, the generally cylindrical set of coil windings having an arcuate or annular central gap that is free of coil windings, the central gap having an axial extent of at least ten centimeters and spanning at least a 180° angular interval, the generally cylindrical set of coil windings further including connecting conductors disposed at each edge of the central gap that electrically connect selected primary and shield coil windings; and
    a main magnet disposed outside of the generally cylindrical set of coil windings and operable to generate an axially oriented static magnetic field in a region of interest surrounded by the generally cylindrical set of coil windings, the generally cylindrical set of coil windings being operable to superimpose a transverse magnetic field gradient on the axially oriented static magnetic field in the region of interest.

2. The magnetic resonance scanner as set forth in claim 1, further comprising:
    a radio frequency coil including a axially oriented conductors disposed in the central gap of the generally cylindrical set of coil windings, the axially oriented conductors disposed in the central gap being substantially axially coextensive with the central gap.

3. The magnetic resonance scanner as set forth in claim 2, wherein the central gap spans an angular interval of at least 180° and less than 360°, there being coil windings disposed over a complementary angular interval not spanned by the central gap, the radio frequency coil further including axially oriented conductors disposed in the complementary angular interval that are axially longer than the central gap.

4. The magnetic resonance scanner as set forth in claim 1, wherein the primary coil windings of the generally cylindrical set of coil windings are disposed at a non-constant radial position over an angular interval not spanned by the central gap to comport with an approximately planar subject support surface.

5. The magnetic resonance scanner as set forth in claim 4, wherein the generally cylindrical set of coil windings is operable to superimpose the transverse magnetic field gradient oriented transverse to the axially oriented static magnetic field at an angle of about 45° respective to the approximately planar subject support surface.

6. The magnetic resonance scanner as set forth in claim 1, wherein the central gap is an annular gap that spaces apart two sub-sets of the generally cylindrical set of coil windings, each sub-set including primary coil windings, shield coil windings at a larger radial position than the primary coil windings, and connecting conductors at the central gap edge electrically connecting selected primary and shield coil windings.

7. The magnetic resonance scanner as set forth in claim 6, further comprising:
    an annular ring of positron emission tomography (PET) detectors disposed in the annular central gap of the generally cylindrical set of coil windings.

8. The magnetic resonance scanner as set forth in claim 7, wherein the annular central gap has an axial extent of at least about fifteen centimeters.

9. The magnetic resonance scanner as set forth in claim 7, further including:
    spaced apart generally cylindrical dielectric formers supporting the two spaced apart sub-sets of generally cylindrical set of coil windings; and
    a brace spanning the central gap to substantially rigidly connect the two spaced apart generally cylindrical dielectric formers;
    wherein the annular ring of PET detectors is vibrationally isolated from a stiff unit defined by the spaced apart generally cylindrical dielectric formers and the brace.

10. The magnetic resonance scanner as set forth in claim 9, further including:
mourning members passing through openings or slots in the brace to support the annular ring of PET detectors independently from the stiff unit defined by the spaced apart generally cylindrical dielectric formers and the brace.

11. The magnetic resonance scanner as set forth in claim 9, further including:
piezo-actuators disposed between the annular ring of PET detectors and the stiff unit defined by the spaced apart generally cylindrical dielectric formers and the brace, the piezo-actuators supporting the annular ring of PET detectors while vibrationally isolating the annular ring of PET detectors from the stiff unit defined by the spaced apart generally cylindrical dielectric formers and the brace.

12. The magnetic resonance scanner as set forth in claim 7, further including:
second order shim coils; and
a shimset controller configured to energize the second order shim coils to shim a magnetic field inhomogeneity introduced by the annular ring of PET detectors.

13. The magnetic resonance scanner as set forth in claim 12, wherein the shimset controller is configured to apply shim currents to the second order shim coils in accordance with an operational shimset calibration when the annular ring of PET detectors is operational, and to apply shim currents to the second order shim coils in accordance with a non-operational shimset calibration when the annular ring of PET detectors is non-operational.

14. The magnetic resonance scanner as set forth in claim 13, wherein the operational shimset calibration shims a relatively smaller PET examination region and the non-operational shimset calibration shims a relatively larger magnetic resonance examination region.

15. The magnetic resonance scanner as set forth in claim 12, wherein the second order shim coils include a three-dimensional shim coil with winding laying in part on each of at least two different cylindrical segments of different radii.

16. A magnetic resonance scanner comprising:
an annular ring of positron emission tomography (PET) detectors;
a generally cylindrical set of coil windings including primary coil windings and shield coil windings at a larger radius than the primary coil windings, the generally cylindrical set of coil windings having an annular central gap receiving the annular ring of PET detectors, the generally cylindrical set of coil windings further including connecting conductors disposed at each edge of the annular central gap that electrically connect selected primary and shield coil windings; and
a main magnet disposed outside of the generally cylindrical set of coil windings and operable to generate an axially oriented static magnetic field in a region of interest surrounded by the generally cylindrical set of coil windings, the generally cylindrical set of coil windings being operable to superimpose a transverse magnetic field gradient on the axially oriented static magnetic field in the region of interest.

17. The magnetic resonance scanner as set forth in claim 16, further including:
mounting members connecting with the annular ring of PET detectors to support the annular ring of PET detectors independently from the generally cylindrical set of coil windings.

18. The magnetic resonance scanner as set forth in claim 16, further including:
piezo-actuators; and
acceleration sensors cooperating with the piezo-actuators to vibrationally isolate the annular ring of PET detectors.

19. The magnetic resonance scanner as set forth in claim 16, wherein the annular central gap of the generally cylindrical set of coil windings has an axial extent of at least about fifteen centimeters.

\* \* \* \* \*